US008555700B2

(12) United States Patent
Dikken (10) Patent No.: US 8,555,700 B2
(45) Date of Patent: Oct. 15, 2013

(54) PARTICULATE FILTER AND METHOD OF USE

(71) Applicant: Measurement Technology Laboratories, LLC, Minneapolis, MN (US)

(72) Inventor: David A. Dikken, Bloomington, MN (US)

(73) Assignee: Measurement Technology Laboratories, LLC, Minneapolis, MN (US)

( * ) Notice: Subject to any disclaimer, the term of this patent is extended or adjusted under 35 U.S.C. 154(b) by 0 days.

(21) Appl. No.: 13/717,328

(22) Filed: Dec. 17, 2012

(65) Prior Publication Data

US 2013/0125623 A1    May 23, 2013

Related U.S. Application Data

(63) Continuation of application No. 12/646,434, filed on Dec. 23, 2009, now abandoned, which is a continuation of application No. 11/060,080, filed on Feb. 16, 2005, now abandoned.

(60) Provisional application No. 60/545,296, filed on Feb. 16, 2004, provisional application No. 60/549,076, filed on Mar. 1, 2004.

(51) Int. Cl.
| | |
|---|---|
| *G01N 1/22* | (2006.01) |
| *G01N 5/00* | (2006.01) |
| *B01D 69/02* | (2006.01) |
| *B01D 69/10* | (2006.01) |

(52) U.S. Cl.
USPC .................. 73/28.04; 73/28.01; 73/865.5

(58) Field of Classification Search
USPC .................. 73/28.01, 28.04, 28.05, 865.5
See application file for complete search history.

(56) References Cited

U.S. PATENT DOCUMENTS

| 4,106,756 A | * | 8/1978 | Rymarchyk et al. ............ 266/99 |
| 4,517,995 A | * | 5/1985 | Lyles ............................ 131/334 |

(Continued)

FOREIGN PATENT DOCUMENTS

| DE | 3126850 | * | 3/1982 |
| EP | 1440298 | * | 4/2008 |

(Continued)

OTHER PUBLICATIONS

"EPA Quality Assurance Guidance Document—Model Quality Assurance Project Plan for the PM2.5 Ambient Air Monitoring Program at Stare and Local Air Monitoring Stations (SLAMS)", United States Environmental Protection Agency—Office of Air Qualtity Planning and Standard, EPA—454/R-98-008, Apr. 1998, pges 1-9.*

(Continued)

*Primary Examiner* — Daniel Larkin
(74) *Attorney, Agent, or Firm* — Christensen Fonder P.A.

(57) ABSTRACT

A particulate filter particularly suited for analytical gravimetric weighing applications is disclosed. The particulate filter includes a polytetrafluoroethylene (PTFE) media supported by a ring and yields stable microgram and submicrogram weighing results. The support ring may be PTFE, metal foil, or another non-hygroscopic polymer such that the mass of the filter does not vary with changes in atmospheric moisture. The filter simplifies the discharge of electrostatic charge buildup such that when a conductive filter media is combined with a conductive ring device, the discharge may be accomplished by placing the filter on a grounded weighing pan or other surface. The particulate filter can simplify filter identification by including identification symbols imprinted on each side of the filter media. Due to the chemically inert qualities of its components, the particulate filter is particularly suited for extraction techniques used during the detection of polycyclic hydrocarbons as is conducted in emissions and ambient air testing.

6 Claims, 4 Drawing Sheets

(56) References Cited

U.S. PATENT DOCUMENTS

| | | | | |
|---|---|---|---|---|
| 4,730,925 A | * | 3/1988 | Chiba et al. | 356/311 |
| 5,238,307 A | * | 8/1993 | Mooney et al. | 383/74 |
| 5,253,476 A | * | 10/1993 | Levendis et al. | 60/279 |
| 5,332,870 A | * | 7/1994 | Strickler | 177/262 |
| 5,766,282 A | * | 6/1998 | Bin | 55/361 |
| 5,830,407 A | * | 11/1998 | Cates | 266/44 |
| 5,863,431 A | * | 1/1999 | Salzburg | 210/474 |
| 6,071,466 A | * | 6/2000 | Cates et al. | 266/44 |
| 6,096,261 A | * | 8/2000 | Anderson et al. | 266/225 |
| 6,125,133 A | * | 9/2000 | Mathur et al. | 373/8 |
| 6,139,310 A | * | 10/2000 | Mahoney et al. | 431/8 |
| 6,142,764 A | * | 11/2000 | Anderson et al. | 431/8 |
| 6,400,747 B1 | * | 6/2002 | Mathur | 373/1 |
| 6,432,163 B1 | * | 8/2002 | Sarma et al. | 75/414 |
| 6,440,355 B1 | * | 8/2002 | Swift | 266/92 |
| 2004/0168429 A1 | * | 9/2004 | Dosaka et al. | 60/275 |
| 2005/0145071 A1 | * | 7/2005 | Cates | 75/382 |

FOREIGN PATENT DOCUMENTS

| | | | |
|---|---|---|---|
| GB | 2150269 | * | 6/1985 |
| JP | 4-323007 | * | 11/1992 |
| JP | 9-201505 | * | 8/1997 |
| JP | 2000-46702 | * | 2/2000 |
| JP | 2002-370020 | * | 12/2002 |
| WO | WO 03/044475 | * | 5/2003 |

OTHER PUBLICATIONS

"Standard Operating Procedure—Gravimetric Analysis of Particulate Collected with R&P Partisol Samplers and MetOne SASS Samplers", State of Oregon—Department of Environmental Quality, DEQ03-LAB-0027-SOP, Version 2.0, Jun. 27, 2003, pp. 1-25.*
Website—www.theairfilterstore.com, Dec. 13, 2003, two pages.*

* cited by examiner

EQUILIBRATE:
- Allow Filters to Acclimate To Ambient Weighing Environment

PRE-WEIGH:
- Scan Barcode on Clean Side of Filter
- Discharge Filter $^{210}Po$ Source of Alpha Particles
- Weigh Filter on Micro-Balance
- Put Filter into Cartridge

ENGINE TEST:
- Scan Barcodes on Load Side of Filter
- Run Engine Test
- Remove Filter From Cartridge

EQUILIBRATE:
- Allow Filters to Acclimate To Ambient Weighing Environment

POST-WEIGH:
- Scan Barcode on Clean Side of Filter
- Discharge Filter Using $^{210}Po$ Source of Alpha Particles
- Weigh Filter on Micro-Balance

FIG. 4

PARTICULATE FILTER AND METHOD OF USE

RELATED APPLICATIONS

This application is a continuation of U.S. patent application Ser. No. 12/646,434, filed Dec. 23, 2009 (now abandoned), which is a continuation of U.S. patent application Ser. No. 11/060,080, filed Feb. 16, 2005 (now abandoned), which claims the benefit of U.S. Provisional Patent Application No. 60/545,296, filed Feb. 16, 2004, and U.S. Provisional Patent Application No. 60/549,076, filed Mar. 1, 2004, which applications are incorporated herein by reference in their entirety.

BACKGROUND OF THE INVENTION

Particulate filters have long been known and widely used. Particulate filters of various types have been utilized for decades in different applications, for example air filtration and analytical measurements in laboratories for a wide range of testing protocols.

Of recent importance is a method of gravimetric analysis. Gravimetric analysis is founded on the principle that a weight of a substance is the elementary measurement used for calculation. In the case of gravimetric analysis of particulate filter applications, the results of a weighing before (pre weighing) and after (post weighing) exposure to an air stream are compared to calculate the load of particulate within the volume of air to which the filter was exposed.

It is important in this calculation that the net load based upon the pre weighing and post weighing data is a result of the trapped particulate and not a variation of the mass of the filter itself. As smaller net loads have been of interest in industry, the requirements for precision and accuracy of the particulate filter gravimetric analysis have been becoming more stringent. Requirements to accurately weigh to the microgram (0.000001 g) level or sub-microgram level (0.0000001 g) are in place in the Code of Federal Regulations for both laboratories responsible for gravimetric fine particulate in the ambient air pollution market comprised of federal, state, county, and local environmental protection agencies, the Combustion Engine Manufacturers and their regulating laboratories, as well as laboratories performing chemical speciation via extraction techniques for the qualification and quantification of the particulate deposited on the filter.

For all interests involved, accurate and precise measurement of particulate filter net load is imperative. To date no known particulate filter has been designed to address specifically improved performance, stability, and usability at the microgram and sub microgram level and for various applications.

SUMMARY OF THE INVENTION

The present invention is directed to a particle sampling test filter. The filter can be used as a particle sampling filter in diesel emissions testing, air quality monitoring and general lab use.

According to one aspect of the invention, a particulate filter comprises a fluoropolymer filter membrane; an identification symbol printed on first and second sides of the filter membrane; and a support ring fused to an outer rim of the filter membrane, wherein the particulate filter is substantially non-hygroscopic and moisture invariable, and substantially inert to dissolution by organic solvents. In one embodiment, the filter membrane comprises a polytetrafluoroethylene (PTFE) material.

According to another aspect of the invention, a method of analytical gravimetric weighing using a particulate filter comprises the steps of equilibrating a particulate filter comprising a fluoropolymer filter membrane and a perfluoroalkoxy polymer support ring to an ambient pre-test environment; identifying the particulate filter by an identification symbol printed on a first and a second side of the particulate filter; dissipating electrostatic charge buildup on the particulate filter; pre-weighing the particulate filter; conducting a testing application using the particulate filter; equilibrating the particulate filter to an ambient post-test environment; identifying the particulate filter by the identification symbol printed on a clean side of the particulate filter; post-weighing the particulate filter; and determining a net load of particulate collected by the particulate filter in the testing application based upon the pre-weighing and the post-weighing.

According to yet another aspect of the invention, a method of detecting polycyclic aromatic hydrocarbons (PAHs) using a particulate filter comprises the steps of identifying a particulate filter comprising a polytetrafluoroethylene filter membrane and a perfluoroalkoxy polymer support ring by an identification symbol printed on a first and a second side of the filter membrane; collecting a particulate sample by the filter; identifying the filter by the identification symbol printed on at least one of the first and second side of the filter membrane; extracting the particulate sample from the filter; and analyzing the extracted sample for PAHs.

According to a further aspect of the invention, a method of manufacturing a particulate filter used for analytical gravimetric weighing comprises the steps of welding or overmolding a support ring comprising a polymer to a filter membrane comprising a fluoropolymer; printing an identification symbol on a first side of the filter membrane; and printing the identification symbol on a second side of the filter membrane offset from the identification symbol on the first side. The polymer of support ring is preferably a fluoropolymer such as perfluoroalkoxy.

The particulate filter and methods of the invention thereby provide various advantages, such as one or more of improved efficiency and permeability, improved moisture stability, improved relative humidity stability, improved static stability, a ringed or ring-less design for improved handling, and the optional functionality of being printable with an identification symbol or code to facilitate automated filter handling and weighing in some embodiments. Embodiments of the particulate filter device of the invention simplify the discharge of electrostatic charge buildup, provide improved identification methods and means, and may be used to accurately measure particulate pollutants and materials.

The above summary of the present invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is directed to a particle sampling test filter that can be used, for example, as a particle sampling filter in diesel emissions testing, and the methodology of use of the particle sampling test filter. The particle sampling filter of the invention provides various advantages, such as one or more of improved efficiency and permeability, improved moisture stability, improved relative humidity stability, improved static stability, a ringed or ring-less design for improved handling, and the optional functionality of being printable with an identification symbol or code to facilitate automated filter handling and weighing in some embodiments. Embodiments of the particulate filter device of the invention simplify the discharge of electrostatic charge buildup, provide improved identification methods and means, and may be used to accurately measure particulate pollutants and materials.

Embodiments of the invention have applicability in a wide range of applications and testing methods, including combustion vehicle emissions testing and analysis. Polycyclic aromatic hydrocarbons (PAHs) are discussed in AGENCY FOR TOXIC SUBSTANCES AND DISEASE REGISTRY, U.S. DEP'T OF HEALTH & HUMAN SERVS., TOXICOLOGICAL PROFILE FOR POLYCYCLIC AROMATIC HYDROCARBONS (1995), which is herein incorporated by reference. PAHs are a group of chemicals formed during the incomplete combustion of coal, oil, gas, wood, garbage, and other organic substances and generally occur as complex mixtures, e.g., as part of combustion products such as soot. Many PAH forms are known carcinogens, one important reason for monitoring their presence and levels in the environment.

PAHs enter the environment most commonly as releases to air from sources such as residential wood burning and exhaust from automobiles and trucks. PAHs in diesel exhaust particulates are dominated by three- and four-ring compounds, primarily fluoranthene, phenanthrene, and pyrene. Diesel exhaust vapor emissions are dominated by phenanthrene and anthracene. Acenaphthene, fluorine, and phenanthrene have been found to be predominant in total (particle- and vapor-phase) diesel emissions. About 90-95% of particulate PAHs are associated with particle diameters less than 3.3 micrometers, with peak distributions localized between 0.4 and 1.1 micrometers. Coarse and nucleic PAH particulate diameters can range overall from less than 0.1 micrometers to more than 5 micrometers. PAH detection and level characterization are typically accomplished using filter sampling methods. Current commercially available particulate filters, however, do not provide the accuracy and ease of handling desired in the industry. Further, known particulate filters do not account for volatilization of support rings. As a result, the use of these particulate filters for PAH sampling may not be entirely accurate. One embodiment of the particulate filter and method of the invention allow for extraction of PAH particulates collected in, for example, vehicle emissions testing.

In one aspect of the invention, parameters have been identified that affect the gravimetric performance of particulate filters from automated laboratory measurements using state of the art redundant weighing processes, robotic automation, and other analytical instrumentation for measuring the environment and other parameters such as electrostatic charge. These parameters include hygroscopic and moisture variability, electrostatic charge, and filter identification, which are discussed below.

With regard to hygroscopic and moisture variability, water from the ambient air is absorbed or discharged from a filter depending upon the ambient moisture content of the laboratory environment in which the weighing occurs. Commercial particulate filters that are currently available generally fail to meet the desired and required accuracy and precision by a factor of five times, resulting in test results that are useless if not detrimental.

With regard to electrostatic charge, media typically used in particulate filters is prone to accumulating electrostatic charge. The effect of this charge is a positive bias on the filter being weighed which can cause significant errors in excess of ten times the desired and required accuracy and precision.

With regard to filter identification, existing filters have either had no identification or an alphanumeric imprint. These approaches force external "carrier tagging" if no identification is present. This practice forces the use of the carriers that are identified by the tagging, and the filter must then be stored or carried in the identified carrier throughout its test life. Even in the case of the alphanumeric imprinted filters, manual data entry or writing is done extensively and is both tedious and prone to errors. Furthermore, the edge printing is obscured when the filters are placed in the cassettes typically used for insertion into air streams.

Various embodiments of the particulate filter of the invention provide reduced hygroscopic variability, improved dissipation of electrostatic charge, enhanced filter identification, and other benefits. These and other aspects of the invention will be described in more detail below in various contexts of the structure and composition of embodiments of the particulate filter, and systems and methods of manufacture, assemblage, and use.

A. Filter Media

The invention can include a fluoropolymer, preferably polytetrafluoroethylene (PTFE), membrane with a polymeric support, such as a polypropylene scrim support. In certain embodiments the test filter has an airflow of at least 1.0 cfm/ft$^2$ at 0.5 inches of water and a thickness of 0.010 inches at 0.5 psi, and more typically at least 2.0 cfm/ft$^2$ at 0.5 inches of water and a thickness of 0.010 inches. The thickness can range from about 0.005 inches to about 0.02 inches. The test filter is generally highly efficient, capturing at least 99 percent of 0.1 µm particles at 10.5 fpm air velocity, more typically at least 99.5 percent of 0.1 µm particles at 10.5 fpm air velocity, and even more desirably 99.99 percent of 0.1 µm particles at 10.5 fpm air velocity.

The polymeric support can comprise, for example, a polypropylene material with a thickness of less than about 0.0100 inches, and typically less than about 0.0045 inches, an air permeability of at least 770 cubic feet per minute per square foot at 0.5 inches of water, and moisture absorption of less than about 1 percent at 65° F. and 65 percent relative humidity.

A suitable polymeric film for use as the membrane includes expanded polytetrafluoroethylene (PTFE) films, as described, for example, in U.S. Pat. Nos. 3,953,566; 4,187, 390; 4,945,125; 5,066,683; 5,157,058; and 5,362,553, each of which is incorporated herein by reference, or available commercially, for example, as Tetratec #1305 (Donaldson Membranes, Philadelphia, Pa.). An expanded PTFE film typically comprises a plurality of nodes interconnected by fibrils to form a microporous structure.

Expanded PTFE films for use in air filtering and other applications often have a relatively good air permeability. One measure of the air permeability of the expanded PTFE films is the number of seconds required for the flow of 100 cubic centimeters of air through the film. Typically, the air permeability of suitable expanded PTFE films is not greater than about 20 seconds, as measured using a Gurley densometer, Model No. 4110, Gurley Precision Instruments, Troy, N.Y. Preferably, the air permeability is not greater than about 6 seconds and, more preferably, not greater than about 4 seconds.

The size of the pores contributes to determining the effective range of particles that can be prevented or restricted from flow through the test filter. Often the average pore size of the membrane is about 2 µm or less. For many filtering applications, the average pore size ranges from about 0.05 µm to about 3.0 µm, preferably, from about 0.2 µm to about 3.0 µm, and, more preferably, from about 1.0 µm to about 2.5 µm. However, larger or smaller average pore sizes may be used.

Another factor in the flow through the filter is the porosity of the membrane, (i.e., the percentage of open space in the volume of the membrane, as determined by comparison of the density of the membrane with respect to the density of non-porous PTFE). Typically, the porosity of the membrane is about 20 percent or greater and about 95 percent or less. Often the porosity of the membrane of a test filter suitable for many filtering applications ranges from about 70 percent to about 95 percent, preferably from about 80 percent to about 95 percent, and more preferably from about 85 percent to about 95 percent.

The support scrim is typically formed using a woven or non-woven porous, polymeric material. Often the support scrim is made using a fibrous material, however, other porous materials may also be used. The average pore size of the support scrim is usually larger than the average pore size of the membrane, although this is not necessary in some applications. The porosity of support scrims suitable for many filtering applications often ranges from about 20 percent to about 80 percent, preferably, from about 30 percent to about 75 percent, and, more preferably, from about 40 percent to about 70 percent.

Suitable polymeric materials for the support scrim include, for example, stretched or sintered plastics, such as polyesters, polypropylene, polyethylene, and polyamides (e.g., nylon). Examples of commercially available non-woven materials for use as a support scrim include Hollytex™ #3257 from Ahlstrom Filtration, Inc. (Mount Holly Springs, Pa.) and Cerex™ #100 from Midwest Filtration Company (Fairfield, Ohio) or Cerex Advanced Fabrics (Pensacola, Fla.). These materials are often available in various weights including, for example, 0.5 oz./sq.yd (about 17 g/m²), 1 oz./sq.yd. (about 34 g/m²), and 2 oz./sq.yd. (about 68 g/m²). Examples of commercially available woven materials for use as a support scrim include a polyester film (Style 604, 150 denier) from Travis Textiles (New York, N.Y.). Additional examples of support scrim materials are various stretched or sintered polyethylene, polypropylene, and other plastics, including, for example, Exxaire XBF-110W, XBF-116W, BF-303W, and BF-513K2 from Exxon Corp. (Buffalo Grove, Ill.), AP3 materials from Amoco Corp. (Atlanta, Ga.), X-7744 Porex T3 from Porex Technologies Corp. (Fairburn, Ga.), and BR-300 from Clopay Building Products Co., Inc. (Cincinnati, Ohio). These same materials may also be used, in some embodiments, as a membrane instead of or in addition to the expanded PTFE membrane.

B. Support Ring

Figure 1:
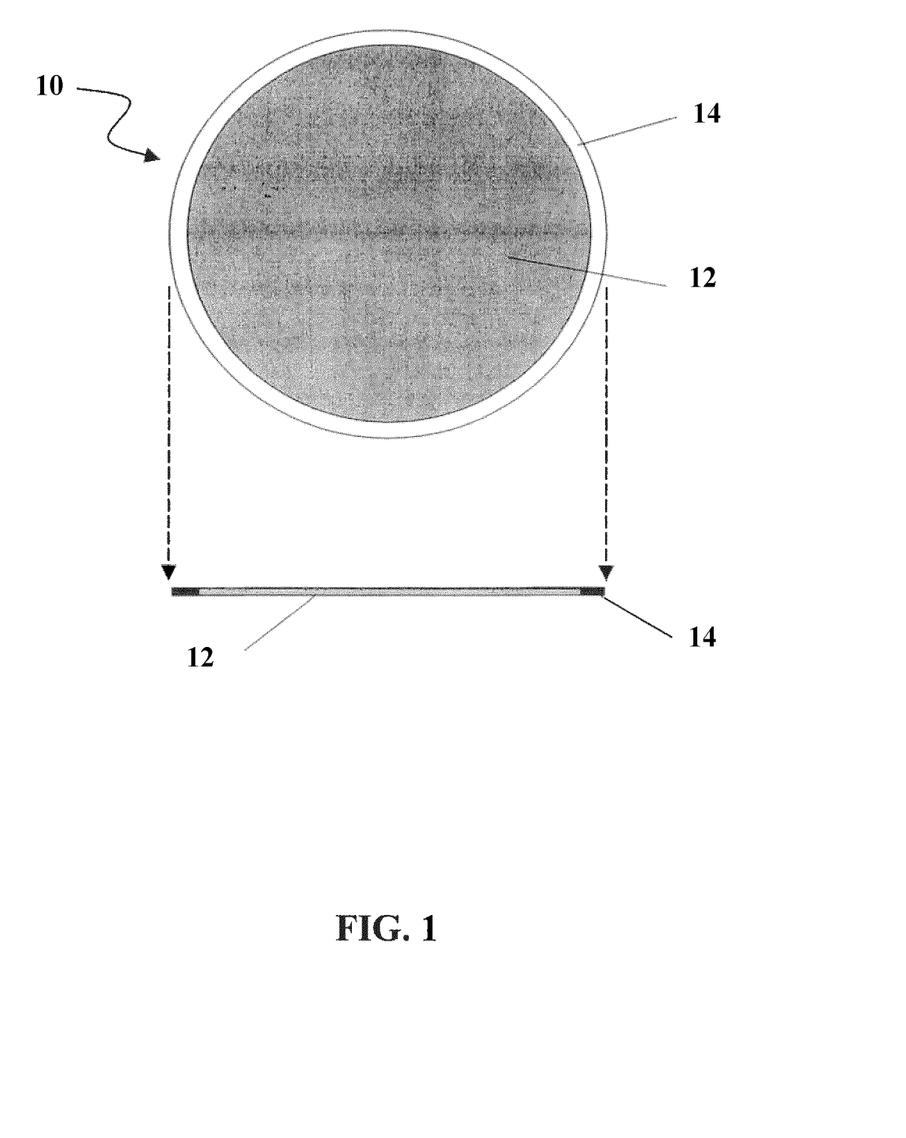
FIG. 1 depicts top and side schematic views of a particulate filter according to one embodiment of the invention.

Referring to FIG. 1, in one embodiment the particulate filter 10 of the present invention comprises a fluoropolymer, for example PTFE, filter membrane 12 supported by a support ring 14. Support ring 14 can be fused or affixed to filter membrane 12 by welding or other methods. Certain embodiments of filter 10 of the present invention thereby provide improved methods of gravimetric analysis, with stable microgram and sub-microgram weighing results. Filter membrane 12 can have a thickness ranging from about 0.0005 inches to about 0.0035 inches, typically about 0.0012 inches.

According to a further implementation of the invention, filter support ring 14 has been identified as one variable affecting hygroscopic variability. Considered broadly, particulate filters are comprised of two classes, including those that have a support structure built into the whole surface as a substrate, as described above, and those that have a membrane supported by a ring for structural integrity. Due to some industry specific interests, particularly in diesel emissions and air quality testing, the supporting ring design is generally desirable. Experimental results have identified that the support ring is one problematic component affecting hygroscopic variability. It is not believed that this was hereto before recognized.

In an embodiment, supporting ring 14 comprises a material whose mass does not vary with changes in atmospheric moisture, for example relative humidity and dew point. Supporting ring 14 may comprise a PTFE or PFA material or other plastic material known to those having skill in the art. In another embodiment, supporting ring 14 comprises a metal foil, for example stainless steel or aluminum. These supporting rings in conjunction with PTFE filter membrane 12 provide a non-hygroscopic filter.

The PFA or other supporting ring material is preferably affixed to the PTFE or other filter membrane by welding or another non-adhesive bonding method. Welding of many fluoropolymers is problematic. It has proven extremely difficult or impossible to weld separate PTFE pieces together, for example, a PTFE filter membrane and a PTFE ring. A PFA ring has proven to be much more amenable to welding to a PTFE filter membrane and is suitably inert and non-hygroscopic. Particular suitable welding techniques include thermal welding and may include ultrasonic welding. Examples of welding techniques for fluoropolymers in the context of tubing and valves are illustrated in U.S. Pat. Nos. 4,929,293 and 6,289,912, both of which are incorporated by reference herein. The polymer of the ring may also be overmolded onto the filter membrane creating a very secure bond between the ring and membrane. The overmolding is a process where the filter membrane, preferably expanded PTFE is placed in a mold having a cavity for the ring. The molten polymer is injected into the ring cavity and contacts the non-molten expanded PTFE thereby bonding to it. The metal rings may be secured to the filter membrane utilizing the adhesive characteristics of these polymers.

Adhesive bonding methods can also be used in some embodiments, for example those having applications in which gravimetric stability and/or particulate extraction are of lesser significance.

Alternative supporting ring materials can include, for example, polymers of tetrafluoroethylene and perfluorovinylether, perfluoroalkoxy (also known as PFA), polymers of tetrafluoroethylene and ethylene (known as ETFE), polyvinylidine fluoride (known as PVDF), polymers of tetrafluoroethylene and hexafluoropropylene (known as FEP), ethylenechlorotnfluoroethylene copolymer (known as ECTFE); polymethylpentene (known as PMP), polyetheretherketone (known as PEEK); polyester, polypropylene, and polyethylene. Certain proprietary polymers also appear suitable for the ring. Namely: Isoplast 2530 from Dow Plastics; Dynaflex® D3204-1000-03 fromGLS Corporation; Vectra A130 from Ticona, and Ryton™ R-4 from Chevron Phillips Chemical Co.

C. Electrostatic Discharge

Specific embodiments of the particulate filter of the invention simplify the discharge of electrostatic charge buildup. The construction of the particulate filter, in particular the construction and composition of the PTFE membrane, can be engineered for electrical conductivity and dissipation in certain embodiments.

A wide variety of materials suitable for compounding with PTFE are generally available, allowing for conductive electrical properties to be varied as needed for particular applications of the invention. These materials include carbon filler, powder or fiber, ceramic materials, and other material known in the art. When a conductive filter membrane is combined with a conductive supporting ring, the particulate filter will allow for electrostatic dissipation when placed on a grounded surface, eliminating the typical necessity of an additional discharging step. For example, weighing pans on precision weighing equipment are generally grounded. This eliminates the need to use Polonium 210 and an alpha emitter radioactive element for electrostatic charge dissipation.

D. Filter Identification

Figure 2:
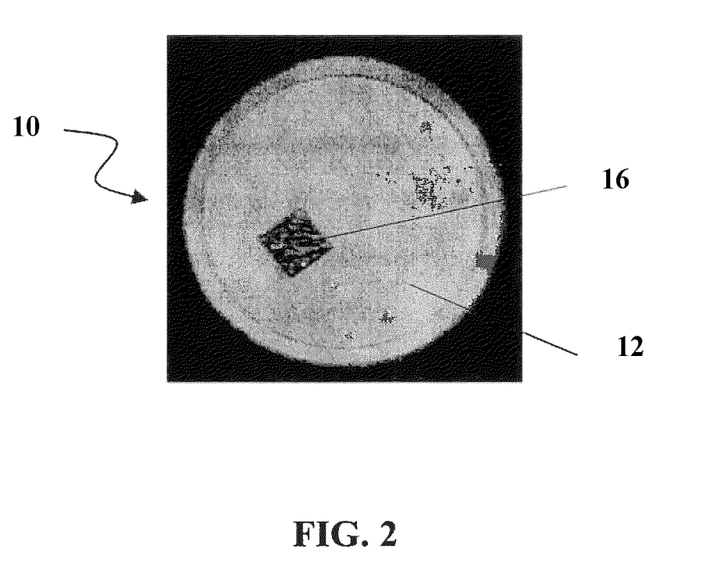
FIG. 2 depicts a top view of particulate filter media having an identification symbol according to one embodiment of the invention.

Various embodiments of the invention also simplify filter identification. Referring to FIG. 2, an identification symbol 16 can be printed on each side of filter membrane 12 near the center of the exposed area. Filter applications in the industry typically leave only one side visible at any time. For example, when filters are placed against a backer plate for support when loaded into airflow streams, the identification must be visible on the "load" side; after loaded, the identification may become obscured by soot, hence the need for a second, clean side identification.

In one embodiment, identification symbols 16 or information codes are printed on both sides of filter membrane 12 and are located off center of each other to preclude the other from interfering with an accurate read. Additionally, to eliminate the misreading of the mirror image information code on the opposite side, the code is designed with a unique start character so as to identify that the symbol or code being read is the target on the facing side and not the mirror image on the opposing side. The identification symbols or information codes are minimally sized so as to provide a negligible effect on filter airflow and mass variability. Identification symbol 16 can be two-dimensional dot coding or bar coding labels, alpha-numeric labels, or other known characters, images, or markings.

Identification symbols 16 are preferably ink printed, for example by an ink jet or similar printing device. The ink or other material used for the identification symbols is selected for stability and chemical properties, in particular for a known or, preferably, lack of affect on gravimetric measurement, chemical speciation via extraction, or other analysis. A known or absent affect of the ink is preferable to streamline post-test extraction and analysis steps and methods. For example, ink with a known or desired chemical profile can be selected. Any ink artifacts extracted with collected particulates or other collected matter can then be easily ignored, aiding in the analysis of particulates of interest. A particular insoluble or permanent ink can also be selected such that the ink does not volatilize or otherwise react with a filter stream, stream component, or collected particulate or other collected matter to produce an extra gaseous or particulate artifact and skew test results. In one embodiment, an ink is selected which is not removed by an extraction solvent, preserving the identification symbol on the filter membrane and maintaining the accuracy and integrity of the test results. Thermal heating of the printed filter membrane during manufacture or otherwise before use can be used to drive off volatiles and ensure mass stability over time.

E. Use of the Test Filter

Figure 3:
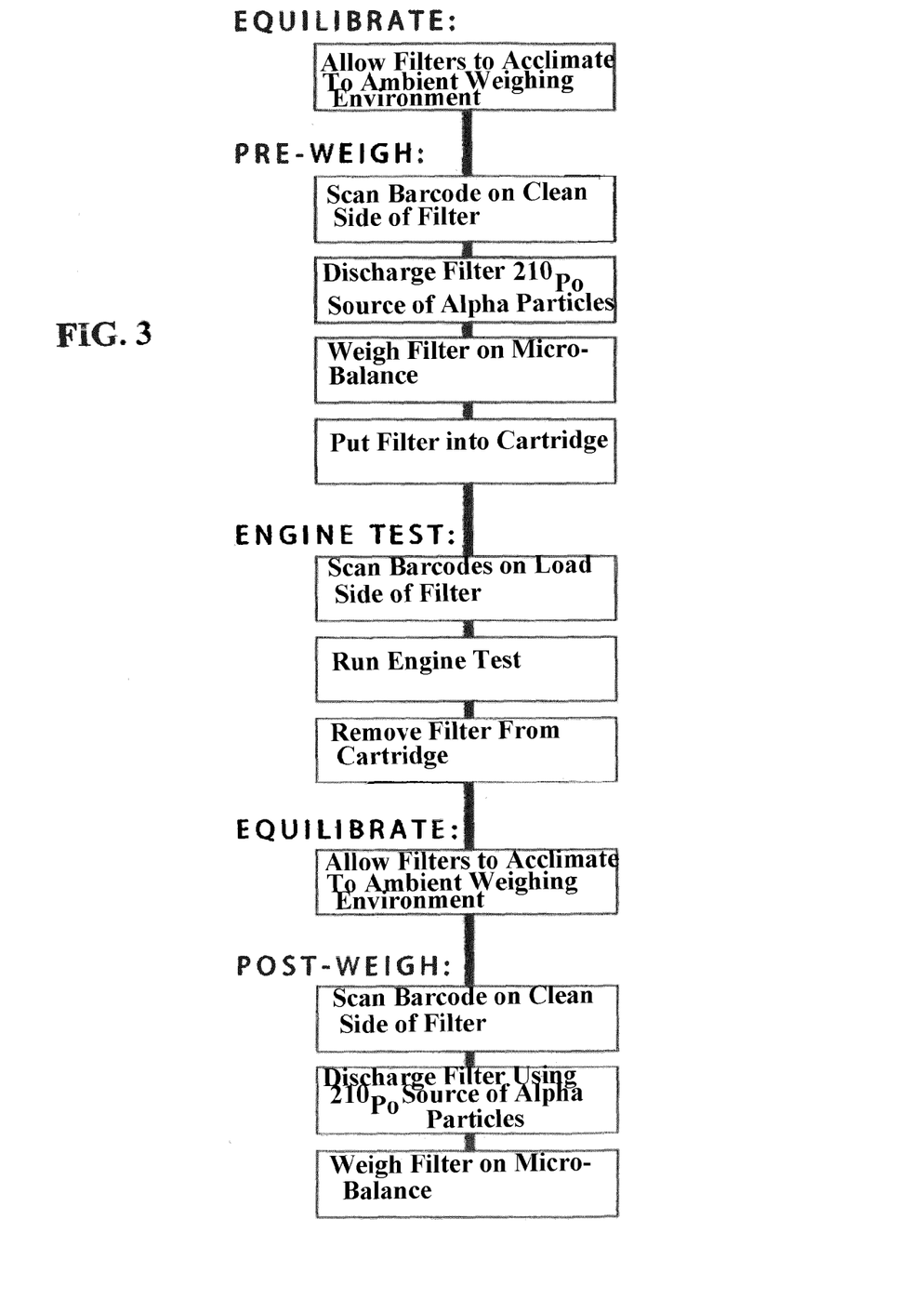
FIG. 3 is a flow chart of a test filter cycle according to one embodiment of the invention.
Figure 4:
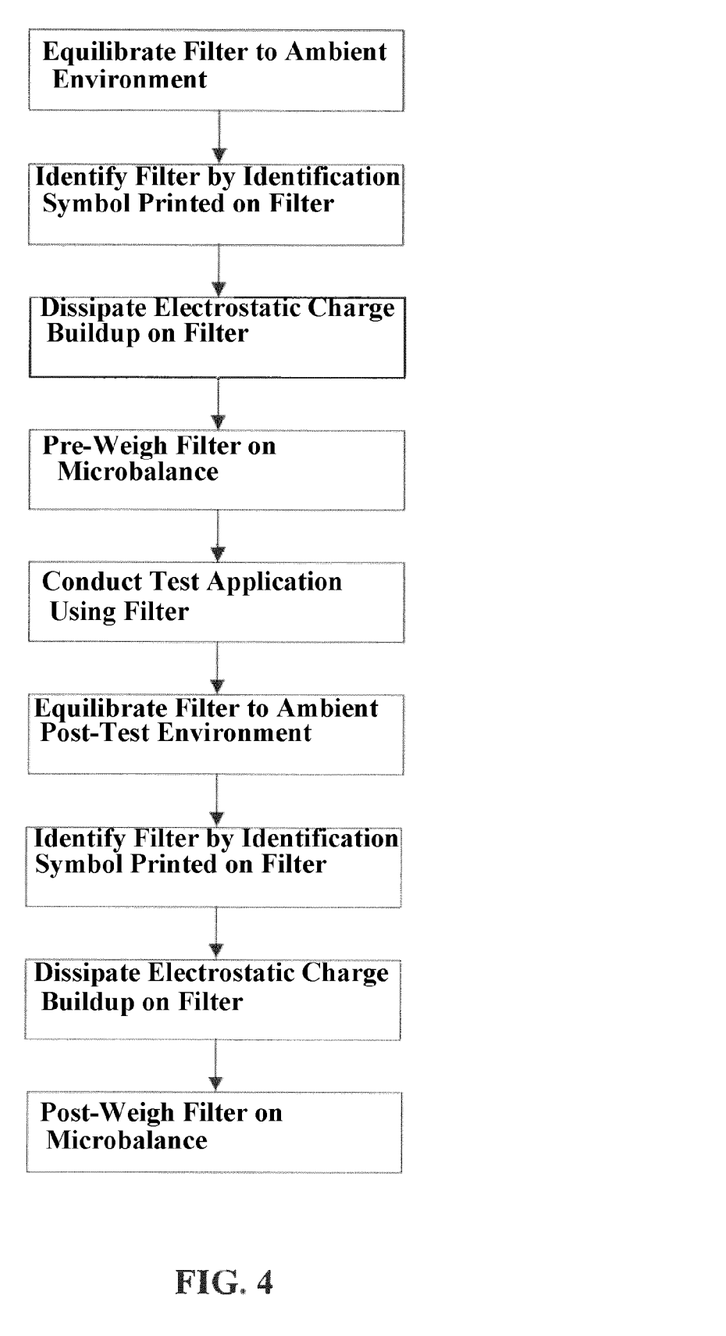
FIG. 4 is a flow chart of a test filter cycle according to one embodiment of the invention.

FIGS. 3 and 4 are flow charts of exemplary life cycles of filter 10, one embodiment of which is also shown in FIGS. 1 and 2. Particulate filter 10 of the invention comprises a filter membrane 12 and non-hygroscopic supporting ring 14, wherein supporting ring 14 is arranged concentrically about filter membrane 12.

As previously described, filter 10 can comprise a PTFE membrane or a similar material. Supporting ring 14 in this improved design can comprise metal foil, PTFE, PFA, or other non-hygroscopic plastic, or similar materials known to those skilled in the art. The material composition, structure, scale, and/or other characteristics of particulate filter 10 can be customized to meet particular standards or requirements for flow rates, size of particle trap, and efficiency, among other characteristics as previously described. For example, filter 10 can be designed to meet a particular industry's standards or to meet a specific set of requirements for an individual application.

Similarly, filter 10 can comprise filter membranes 12 and supporting rings 14 of various sizes and shapes. Filter 10 can have various dimensions and shapes, but in certain embodiments is a circle of less than 100 mm diameter, alternatively less than 75 mm in diameter, and desirably less than 50 mm diameter. In one embodiment, the filter has a diameter of 47 mm. A suitable size of filter 10 is about 46.2 millimeters (mm) in diameter with a 3 mm wide concentric supporting ring 14 around the rim. Supporting ring 14 can be welded, bonded, adhered, or fused onto one but preferably both sides of filter membrane 12 around supporting ring 14, as described in more detail above. Supporting ring 14 can be affixed to filter membrane 12 by other methods and means according to a desired use or application, for example by adhering, crimping, or otherwise joining. The size and thickness of supporting ring 14 can also vary for particular applications and embodiments.

Filter 10 is substantially flat in some embodiments, although the thickness can vary overall or in portions depending upon need or application. To facilitate weighing and other applications known in the art, one example embodiment of particulate filter 10 is less than about 7 millimeters from flat over the entire surface. For example, filter membrane 12, excluding supporting ring 14, is about 2 microns thick in one embodiment.

Filter 10 of the invention can also include identification information. In use, only one side of filter 10 is typically labeled with an identifier and visible. If the labeled side becomes obscured during use by particulate that collects on filter 10, for example soot or other debris, correctly identifying filter 10 after use becomes difficult if not impossible.

Referring to the embodiment of FIG. 2, filter 10 is labeled with an identification symbol 16, for example a two-dimensional dot-coding identification symbol, on each side of filter membrane 12 before use. Identification symbol 16 can be located on membrane 12 so as to provide a negligible effect on airflow and mass variability.

Particulate filter 10 preferably comprises a material whose mass does not vary with changes in atmospheric moisture, for example relative humidity and dew point. It is generally desired in the industry that an air filter minimize the change in the amount of retained moisture with respect to changing atmospheric moisture conditions in order to provide accurate, precise, and stable results. With such a filter, the difference between a filter's weight after it has been used and its weight prior to being used can therefore more accurately be attributed to the material absorbed onto the filter, rather than to differences in atmospheric moisture content between the pre-test and post-test weighings.

For example, moisture variation effect on mass may be less than or approximately 0.4 micrograms per approximately 1% ambient humidity change with constant temperature to about ±0.1° C. on filters in the mass range of approximately 0.140 grams to approximately 0.160 grams, which are generally 47 mm filters. The moisture variation for other filter sizes is generally proportional to the filter mass.

Example embodiments of the particulate filter of the present invention have an improved hygroscopic absorption rate. For example, one embodiment of the particulate filter provided a hygroscopic absorption rate of less than about 0.4 micrograms per percentage relative humidity, as opposed to commercially available filters which preferably have hygroscopic variation in excess of ten times this absorption rate.

Accordingly, and referring in particular to FIG. 3, the filter is first acclimated to the ambient weighing environment. Next, in pre-weigh preparation, the filter is identified, for example by scanning an identification symbol on the clean side of the filter in an embodiment. Any electrostatic charge on the filter is dissipated by placing the filter on a grounded surface, for example a weighing pan, or by using a Polonium 210 source of alpha particles. The filter then is weighed on a micro-balance and loaded into a cartridge.

In a particular application, which can be an engine test, an identification symbol on a load side of the filter is charged, the engine test is run, and the filter is removed from the cartridge. After the filter has acclimated to the ambient weighing environment, the post-weigh procedure is performed. The filter is identified by scanning the identification symbol on the clean side of the filter, the filter is electrostatically discharged, and the filter is weighed on a micro-balance for the post-test weight. Another test method is shown in FIG. 4.

A particulate filter according to one embodiment of the invention can have applicability in methods for detecting PAHs, nitro-PAHs, and other relevant particulates. Sampling methods that collect PAHs can include use of embodiments of the particulate filter of the present invention, as the particulate filter allows for improved, i.e., more accurate, extraction of PAH and nitro-PAH emissions. In one embodiment, the method comprises the steps of collecting particulate emissions by a non-hygroscopic particulate filter having an inert or nearly inert filter ring, extracting the particulate emissions from the particulate filter, cleaning the extracts, and analyzing the extracts.

In one embodiment, the step of collecting particulate emissions comprises exposing the particulate filter to an air stream, more particularly to an exhaust stream and more particularly still to an automotive exhaust stream. Embodiments of the invention can therefore provide more accurate air testing results, such as in diesel and other vehicle emissions testing for PAHs, nitro-PAHs, and ambient air quality testing. In one embodiment, the particulate filter comprises a PTFE filter membrane and a PFA supporting ring. The step of extracting the particulate emissions comprises Soxhlet extracting the particulate emissions from the particulate filter. While numerous extraction methods are available, for example Soxhlet, ultrasonic, and microwave, among others, many involve the use of organic solvents. The PTFE filter membrane and PFA support ring of this embodiment are nearly inert to extraction process solvents, and an ink used to print identification symbols on the filter can be selected for having a known chemical profile, for being insoluble to a particular solvent, and/or for having a nonvolatile affect on a test stream, as described above. Typical organic solvents used for extraction include dichloromethane, acetone, toluene, cyclohexane, hexane, an ethanol/toluene mixture, benzene, methylenechloride, methanol, and various mixtures of these as well as other solvents. The step of analyzing the extracts can comprise analyzing by gas chromatography/mass spectrometry/selective ion monitoring (GC/MS/SIM) in positive ion electron impact mode for PAHs and analyzing by GC/MS/SIM runs in negative ion chemical ionization mode for nitro-PAHs. In the case of a soluble ink having a known chemical profile, the step of analyzing the extracts further comprises identifying and ignoring the extracted ink.

The invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

What is claimed:

1. A method of analytical gravimetric weighing using a particulate filter comprising the steps of: equilibrating a circular particulate filter with a circular periphery and a non-hygroscopic support ring comprising a filter membrane comprising a fluoropolymer to an ambient pre-test environment; identifying the particulate filter by scanning an identification symbol pre-printed on a first and a second side directly on the filter membrane of the particulate filter; dissipating electrostatic charge buildup on the particulate filter; pre-weighing the particulate filter; conducting a testing application using the particulate filter; equilibrating the particulate filter to an ambient post-test environment; identifying the particulate filter by the identification symbol pre-printed on a clean side of the particulate filter media by scanning the identification symbol; post-weighing the particulate filter; and determining a net load of particulate collected by the particulate filter in the testing application based upon the pre-weighing and the post-weighing.

2. The method of claim 1, further comprising the step of selecting polytetrafluoroethylene as the fluoropolymer material.

3. The method of claim 1, further comprising the steps of: exposing the particulate filter to a volume of air in the testing application; and calculating a load of particulate within the volume of air from the net load of particulate collected.

4. The method of claim 1, wherein the step of dissipating electrostatic charge buildup on the particulate filter comprises placing the particulate filter on a grounded surface.

5. The method of claim 1, wherein the step of dissipating electrostatic charge buildup on the particulate filter comprises using Polonium 210 or another alpha emitter radioactive element.

6. The method of claim 1, wherein the step of conducting a testing application using the particulate filter comprises conducting an engine test to detect a polycyclic aromatic hydrocarbon.

* * * * *